United States Patent
Foster et al.

(10) Patent No.: US 9,863,865 B2
(45) Date of Patent: Jan. 9, 2018

(54) CELL SORTING SYSTEM USING ELECTROMAGNETIC SOLENOID

(71) Applicant: Owl biomedical, Inc., Goleta, CA (US)

(72) Inventors: John S Foster, Santa Barbara, CA (US); Nicholas C. Martinez, Santa Barbara, CA (US); Daryl W. Grummitt, Santa Barbara, CA (US); Ralf-Peter Peters, Bergisch Gladbach (DE); Christian Peth, Düsseldorf (DE); Markus Nagel, Frechen (DE)

(73) Assignee: Owl biomedical, Inc., Goleta, CA (US)

( * ) Notice: Subject to any disclaimer, the term of this patent is extended or adjusted under 35 U.S.C. 154(b) by 112 days.

(21) Appl. No.: 14/634,909

(22) Filed: Mar. 2, 2015

(65) Prior Publication Data

US 2015/0177122 A1    Jun. 25, 2015

Related U.S. Application Data

(63) Continuation-in-part of application No. 13/998,095, filed on Oct. 1, 2013, now Pat. No. 9,372,144.

(51) Int. Cl.
*G01N 15/14* (2006.01)
*B01L 3/00* (2006.01)
*F16K 99/00* (2006.01)

(52) U.S. Cl.
CPC .... *G01N 15/1484* (2013.01); *B01L 3/502738* (2013.01); *B01L 3/502761* (2013.01); *F16K 99/0011* (2013.01); *F16K 99/0028* (2013.01); *F16K 99/0046* (2013.01); *B01L 2200/0652* (2013.01); *B01L 2300/0654* (2013.01); *B01L 2300/0864* (2013.01); *B01L 2400/0622* (2013.01); *B01L 2400/0633* (2013.01); *B01L 2400/0644* (2013.01);

(Continued)

(58) Field of Classification Search
CPC ..... B01L 2200/0652; B01L 2300/0654; B01L 2300/0864; B01L 2400/0622; B01L 2400/0633; B01L 2400/0644; B01L 3/502738; B01L 3/502761; F16K 2099/0084; F16K 2099/0086; F16K 99/0028; F16K 99/0046; G01N 15/1484; G01N 2015/149
See application file for complete search history.

(56) References Cited

U.S. PATENT DOCUMENTS

| 6,838,056 B2 | 1/2005 | Foster |
| 6,941,005 B2 | 6/2005 | Lary et al. |
| 7,264,972 B2 | 4/2007 | Foster |

(Continued)

OTHER PUBLICATIONS

U.S. Appl. No. 13/374,899, filed Jan. 23, 2012, Foster et al.
U.S. Appl. No. 13/374,898, filed Jan. 23, 2012, Foster et al.

*Primary Examiner* — Samuel P Siefke
(74) *Attorney, Agent, or Firm* — Jaquelin K. Spong

(57) ABSTRACT

A MEMS-based cell sorting system is disclosed, which uses a novel combination of features to accomplish the cell sorting in the microfabricated channels housed in a disposable cartridge. The MEMS-based cell sorting system may include a microfabricated cell sorting valve that is responsive to an applied magnetic field. The MEMS-based cell sorting system may further include an electromagnet that generates a magnetic field to actuate the microfabricated cell sorting valve. The electromagnet may have a design which allows it to create a very localized magnetic field while having adequate thermal properties to operate reliably.

20 Claims, 12 Drawing Sheets

(52) U.S. Cl.
CPC .............. *F16K 2099/0084* (2013.01); *F16K 2099/0086* (2013.01); *G01N 2015/149* (2013.01)

(56) References Cited

U.S. PATENT DOCUMENTS

| | | |
|---|---|---|
| 7,220,594 B2 | 5/2007 | Foster et al. |
| 7,229,838 B2 | 12/2007 | Foster et al. |
| 7,569,789 B2 | 8/2009 | Hayenga et al. |
| 7,745,221 B2 | 6/2010 | Butler et al. |
| 8,120,770 B2 | 2/2012 | Huang et al. |
| 2009/0014360 A1 | 1/2009 | Toner et al. |
| 2009/0092509 A1 | 4/2009 | Barbic et al. |
| 2012/0190104 A1 | 7/2012 | Foster et al. |
| 2014/0034555 A1 | 2/2014 | Foster et al. |

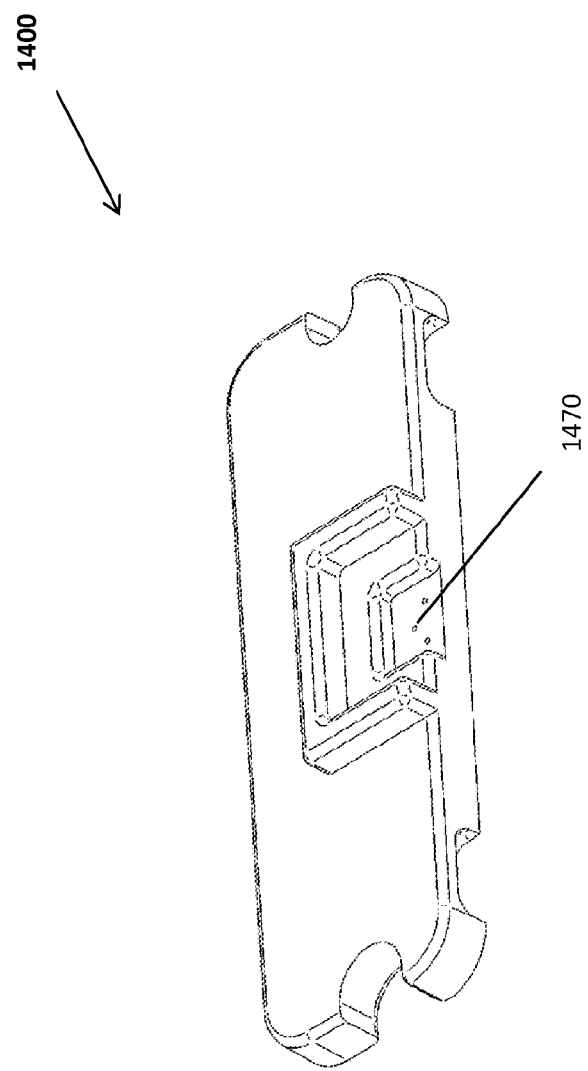

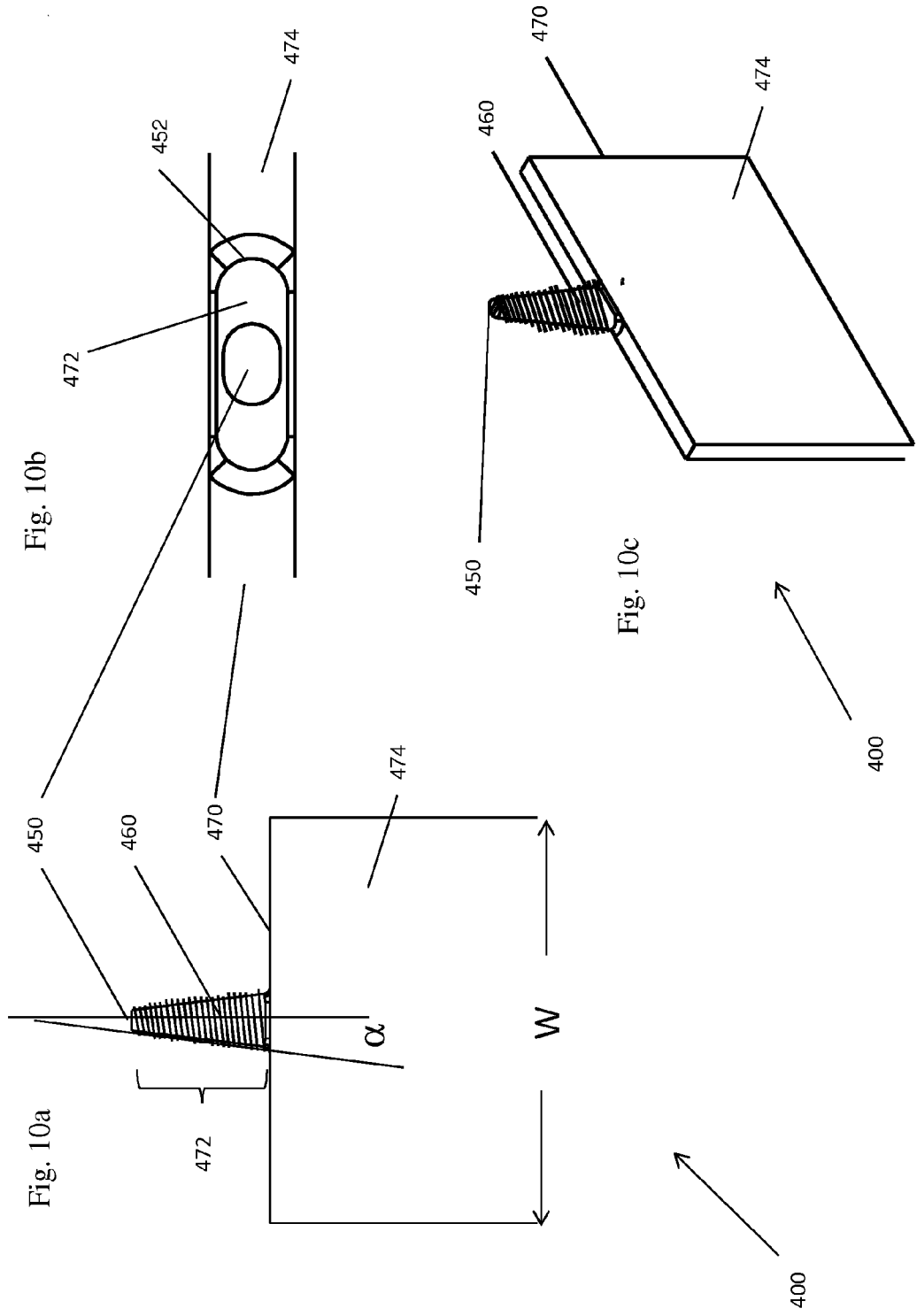

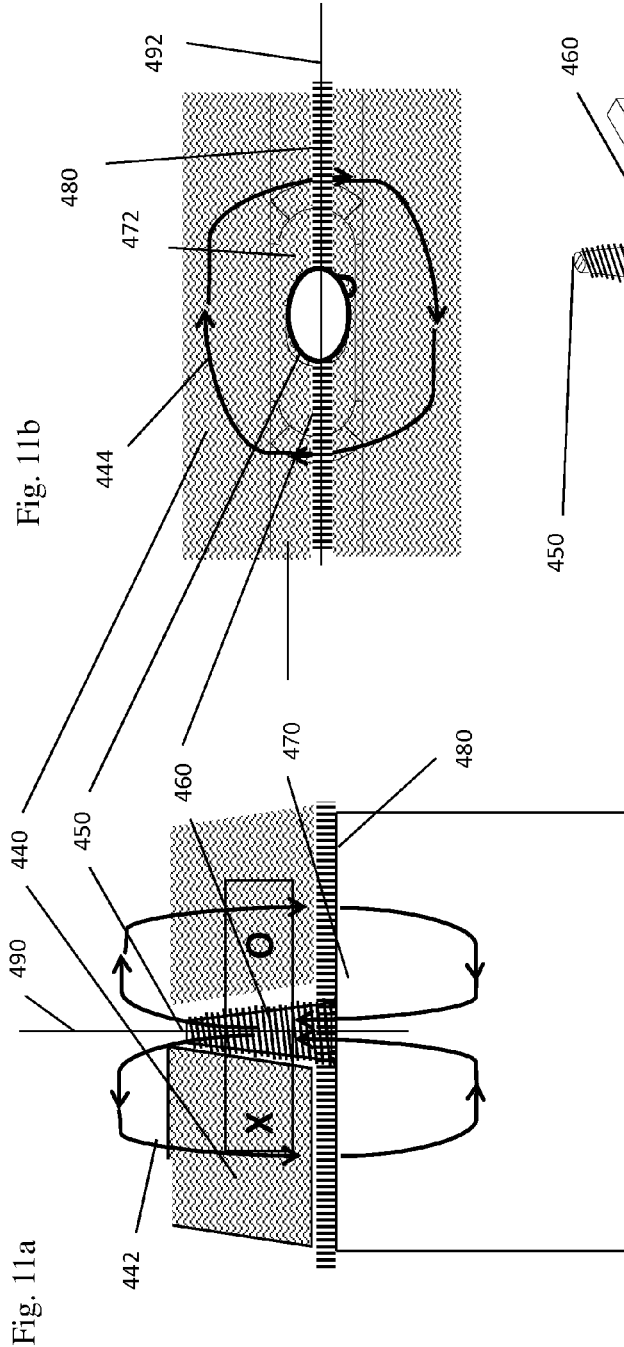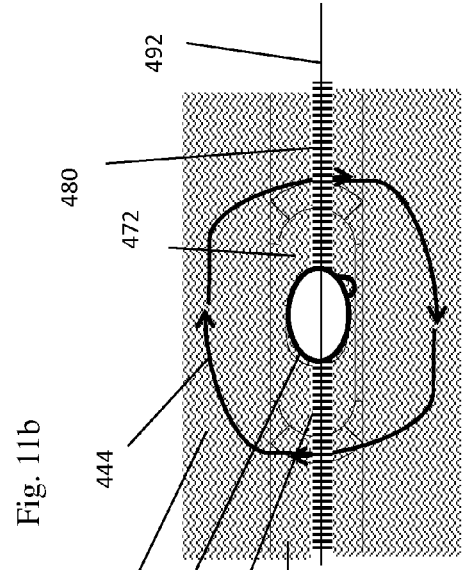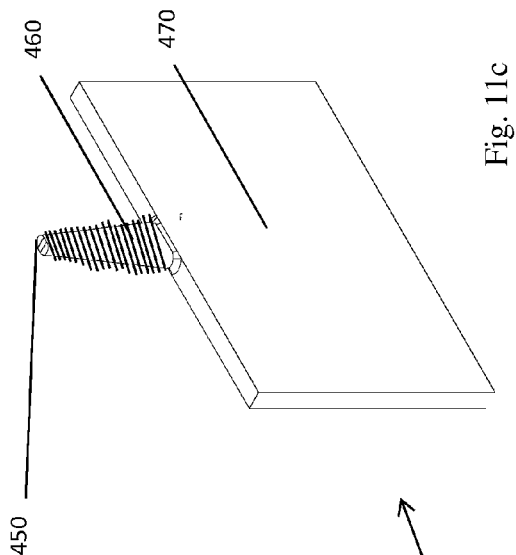

CELL SORTING SYSTEM USING ELECTROMAGNETIC SOLENOID

CROSS REFERENCE TO RELATED APPLICATIONS

This US Patent Application is a continuation-in-part of U.S. patent application Ser. No. 13/998,095, filed Oct. 1, 2013, which is incorporated by reference herein in its entirety.

STATEMENT REGARDING FEDERALLY SPONSORED RESEARCH

Not applicable.

STATEMENT REGARDING MICROFICHE APPENDIX

Not applicable.

BACKGROUND

This invention relates to a cell sorting system using a microfabricated, movable cell sorting mechanism.

Microelectromechanical systems (MEMS) are very small, often moveable structures made on a substrate using surface or bulk lithographic processing techniques, such as those used to manufacture semiconductor devices. MEMS devices may be moveable actuators, sensors, valves, pistons, or switches, for example, with characteristic dimensions of a few microns to hundreds of microns. A moveable MEMS switch, for example, may be used to connect one or more input terminals to one or more output terminals, all microfabricated on a substrate. The actuation means for the moveable switch may be thermal, piezoelectric, electrostatic, or magnetic, for example. MEMS devices can also be made which manipulate particles passing by the MEMS device in a fluid stream.

For example, a MEMS device may be a movable valve, used as a sorting mechanism for sorting various particles from a fluid stream, such as cells from blood. The particles may be transported to the sorting device within the fluid stream enclosed in a microchannel, which flows under pressure. Upon reaching the MEMS sorting device, the sorting device directs the particles of interest such as a blood stem cell, to a separate receptacle, and directs the remainder of the fluid stream to a waste receptacle.

Previously, particle sorters existed using fluorescence-activated cell sorting (FACS) and are known as flow cytometers. Flow cytometers are generally large and expensive systems which sort cells based on a fluorescence signal from a tag affixed to the cell of interest. The cells are diluted and suspended in a sheath fluid, and then separated into individual droplets via rapid decompression through a nozzle. After ejection from a nozzle, the droplets are separated into different bins electrostatically, based on the fluorescence signal from the tag. Among the issues with these systems are cell damage or loss of functionality due to the decompression, difficult and costly sterilization procedures between samples, inability to re-sort sub-populations along different parameters, and substantial training necessary to own, operate and maintain these large, expensive pieces of equipment. For at least these reasons, use of flow cytometers has been restricted to large hospitals and laboratories and the technology has not been accessible to smaller entities.

MEMS-based cell sorting systems may have substantial advantages over flow cytometers in terms of cost, speed and size. A number of patents have been granted which are directed to such MEMS-based particle sorting devices. For example, U.S. Pat. No. 6,838,056 (the '056 patent) is directed to a MEMS-based cell sorting device, U.S. Pat. No. 7,264,972 b1 (the '972 patent) is directed to a micromechanical actuator for a MEMS-based cell sorting device. U.S. Pat. No. 7,220,594 (the '594 patent) is directed to optical structures fabricated with a MEMS cell sorting apparatus, and U.S. Pat. No. 7,229,838 (the '838 patent) is directed to an actuation mechanism for operating a MEMS-based particle sorting system. Additionally, U.S. patent application Ser. No. 13/374,899 (the '899 application) and Ser. No. 13/374,898 (the '898 application) provide further details of other MEMS designs. Each of these patents ('056, '972, '594 and '838) and patent applications ('898 and '899) is hereby incorporated by reference.

Among the problems encountered with using microfluidic devices in the cell sorting systems as mentioned above, is the clogging of the narrow passageways, and the interface of these narrow passageways with the macroscopic world, and control of the movement of these very small, movable devices.

SUMMARY

A cell sorting system is described which makes use of a microfabricated cell sorting MEMS chip. The passageways in the MEMS chip are formed lithographically, and are thus very small. Clogging of these narrow passageways presents a significant challenge to reliable, long term operation. Additionally, these narrow passageways must be mated to much larger, macroscopic features, and handle small volumes of fluids, particularly when sorting rare cells.

In the system described here, a various novel design elements are brought to bear to enable such a MEMS cell sorting system. A plastic interposer is used to provide the interconnections between the microscopic passages and the macroscopic features. A specially designed electromagnet provides the precisely located electromagnetic fields which cause the very small MEMS chip to move within the much larger system. This electromagnet minimizes heat produced, and thus improves efficiency. Finally, a special formulation of fluid materials is used to reduce or eliminate clogging.

Accordingly, a cell sorting system is described, which may include a cell sorting valve microfabricated on a silicon substrate with microfabricated channels leading from the cell sorting valve, a disposable cartridge containing a sample reservoir, a sort reservoir and a waste reservoir and an interposer that links the microfluidic passages in silicon substrate to the reservoirs in the disposable cartridge.

Accordingly, the cell sorting valve may be quite small, and may be actuated magnetically. In order to provide the actuating magnetic field, the cell sorting system may further include an electromagnet with a tapered tip, coils and magnetic core, wherein the tapered shape serves to concentrate the lines of flux produced by the coils and core, and exit from the electromagnet in the vicinity of the tip. The tapered tip and magnetic core may have a particular shape and dimensions, and may be embedded in a heat sinking material to improve performance.

BRIEF DESCRIPTION OF THE DRAWINGS

Various exemplary details are described with reference to the following figures, wherein:

FIG. 9 is a perspective view of the obverse side of the exemplary interposer;

FIG. 10a is a plan view of the targeted electromagnet that may generate the magnetic field which may actuate the MEMS chip sorter from the first position (FIG. 1) to the second position (FIG. 2); FIG. 10b is a top-down view of the magnet tip; FIG. 10c is a perspective view of the targeted electromagnet;

FIG. 11a is a plan view of a second embodiment of the targeted electromagnet that uses a heatsinking material; FIG. 11b is a top-down view of the second embodiment of the magnet tip; FIG. 11c is a perspective view of the second embodiment of the targeted electromagnet.

It should be understood that the drawings are not necessarily to scale, and that like numbers may refer to like features.

DETAILED DESCRIPTION

Systems and methods are described for sorting target particles from non-target materials in a fluid stream. The systems and methods make use of a microfabricated (MEMS) movable valve or sorting mechanism, which directs the target particle from a sample input passageway into a sort passageway, while allowing non-target material to flow into a waste passageway. Both passageways lead to a separate, respective reservoir, the sort and waste reservoir, and are stored there until removal. The sort, sample and waste reservoirs, along with the MEMS chip sorter, may be contained in a plastic disposable cartridge. This cartridge may then be discarded after the fluids are collected from the reservoirs. This allows greatly reduced burden for sterilizing the system between samples. The systems and methods may also have significant advantages in terms of cost, performance, speed and complexity. The system may also be substantially gentler in its handling of cells, such that viability of cells in the effluent is greatly improved compared to droplet-based flow cytometers.

Because of the microfluidic nature of this cell sorting system, measures are taken to reduce or eliminate clogging, and to handle the small volumes of fluids, and to control the very small movable valve. An interposer may be used to provide the interconnections between the microscopic passages and the macroscopic features. Finally, specially designed electromagnet provides the precisely located electromagnetic fields which cause the very small MEMS chip to move within the much larger system. This electromagnet minimizes heat produced, and thus improves efficiency. Each of these features is described further below.

Figure 1:
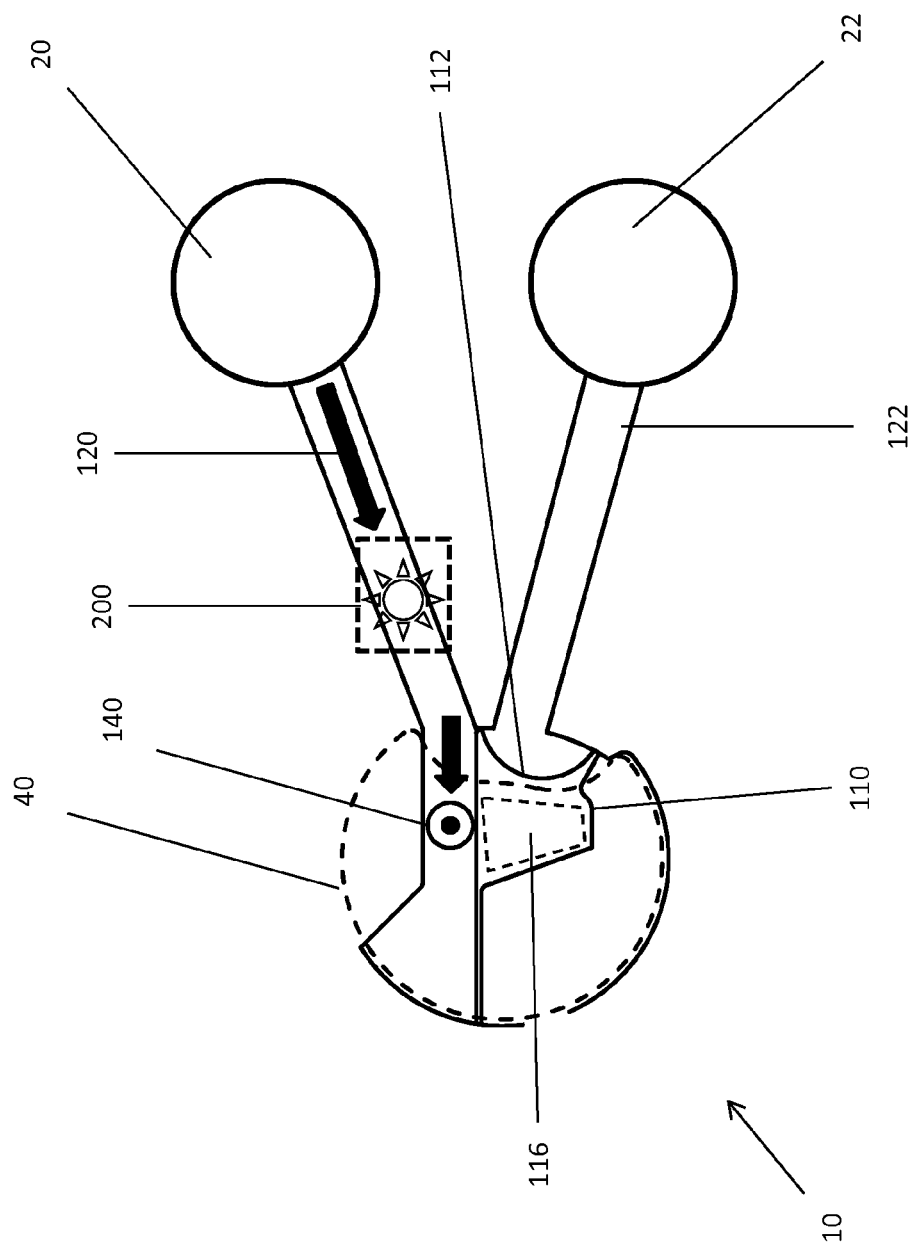
FIG. 1 is a schematic illustration of a MEMS chip sorter in a first position.

FIG. 1 is a schematic diagram of a microfabricated cell sorting mechanism, MEMS chip sorter 10, which may be used in the particle sorting system described here. Details of cell sorting mechanism may be found in co-pending U.S. patent application Ser. No. 13/998,095, (hereinafter the '095 patent application) incorporated by reference herein. Among the unique features of microfabricated cell sorting mechanism 10 is that the motion of the cell sorting valve 110 is parallel to the fabrication plane of the valve. In addition, the waste channel 140 is substantially orthogonal to the sample inlet channel 120 and the sort output channel 122. These features enable distinct advantages in terms of speed and precision, valve throughput and ease of the microfluidic sorting.

In the plan view illustration of FIG. 1, the novel MEMS chip sorter 10 is in the quiescent (un-actuated) position. The MEMS chip sorter 10 may include a microfabricated fluidic valve or movable member 110 and a number of microfabricated fluidic channels 120, 122 and 140. The fluidic valve 110 and microfabricated fluidic channels 120, 122 and 140 may be formed in a suitable substrate, such as a silicon substrate, using MEMS lithographic fabrication techniques as described in greater detail in the '095 application. The fabrication substrate may have a fabrication plane in which the device is formed and in which the movable member 110 moves.

A sample stream may be introduced to the microfabricated fluidic valve 110 by a sample inlet channel 120. The sample fluid may be stored in a sample reservoir 20 prior to sorting by fluidic valve 110. The sample stream may contain a mixture of particles, including at least one desired, target particle and a number of other undesired, non-target particles. The particles may be suspended in a fluid. For example, the target particle may be a biological material such as a stem cell, a cancer cell, a zygote, a protein, a T-cell, a bacteria, a component of blood, a DNA fragment, for example, suspended in a buffer fluid such as saline, or the novel chemistry described below. The inlet channel 120 may be formed in the same fabrication plane as the valve 110, such that the flow of the fluid is substantially in that plane. The motion of the valve 110 is also within this fabrication plane. The decision to sort/save or dispose/waste a given particle may be based on any number of distinguishing signals. In one exemplary embodiment, the decision is based on a fluorescence signal emitted by the particle, based on a fluorescent tag affixed to the particle and excited by an illuminating laser. Laser interrogation region 200 is the portion of the microfluidic passageway in which an illuminating or interrogating laser is directed on the target particle, in order to distinguish it from the other constituents of the fluid sample. Details as to this detection mechanism are well known in the literature, and further discussed below with respect to FIG. 3. However, other sorts of distinguishing signals may be anticipated, including scattered light or side scattered light which may be based on the morphology of a particle, or any number of mechanical, chemical, electric or magnetic effects that can identify a particle as being either a target particle, and thus sorted or saved, or an non-target particle and thus rejected or otherwise disposed of.

With the valve 110 in the position shown, the input stream passes unimpeded to an output orifice and channel 140 which is out of the plane of the inlet channel 120, and thus out of the fabrication plane of the MEMS chip sorter 10. That is, the flow is from the inlet channel 120 to the output orifice 140, from which it flows substantially vertically, and thus orthogonally with respect to the inlet channel 120. This output orifice 140 leads to an out-of-plane channel that may be perpendicular to the plane of the paper showing FIG. 1. More generally, the output channel 140 is not parallel to at least one of the plane of the inlet channel 120 or sort channel 122, or the fabrication plane of the movable member 110.

The output orifice 140 may be a hole formed in the fabrication substrate, or in a covering substrate that is bonded to the fabrication substrate. Further, the valve 110 may have a curved diverting surface 112 which can redirect the flow of the input stream into a sort output stream. The contour of the orifice 140 may be such that it overlaps some, but not all, of the inlet channel 120 and sort channel 122. By having the contour 140 overlap the inlet channel, a route exists for the input stream to flow directly into the waste orifice 140 when the movable member or valve 110 is in the un-actuated waste position. The waste channel 140 may lead to a waste reservoir 40, which may collect the non-target material.

Figure 2:
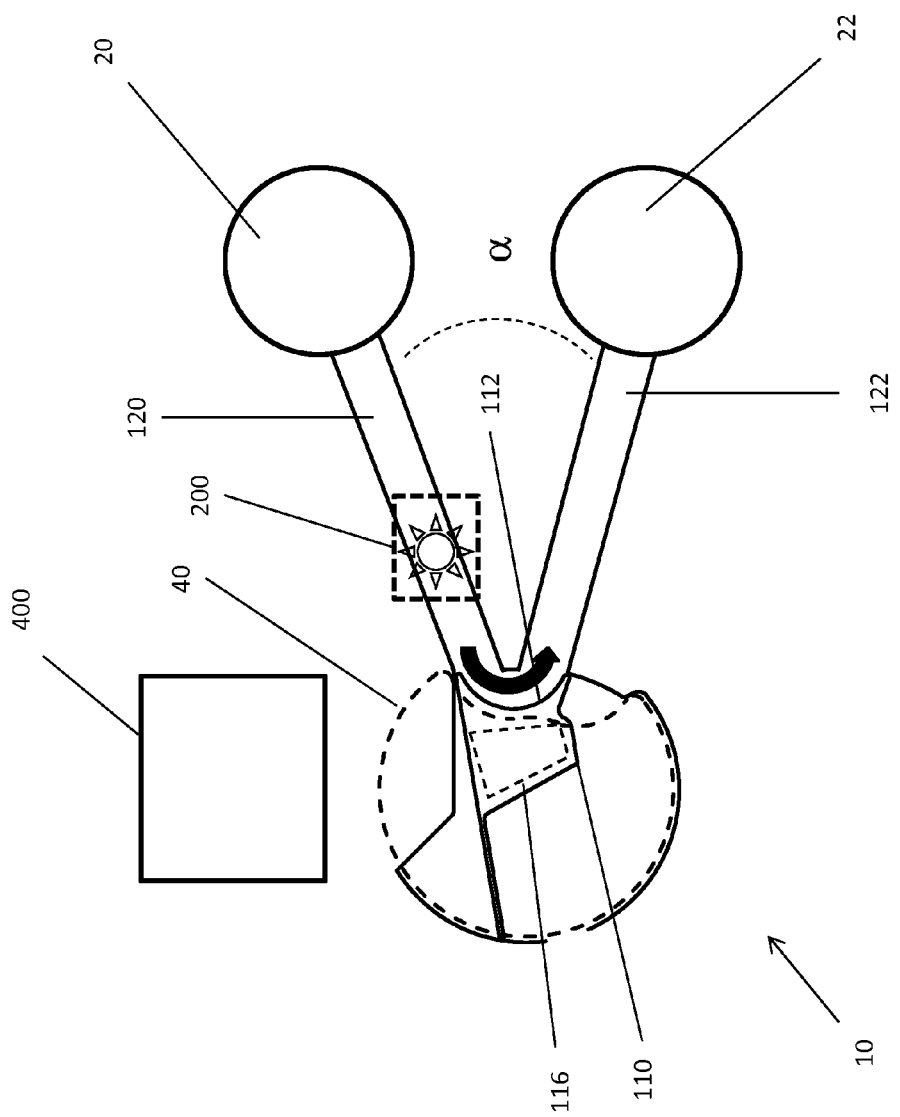
FIG. 2 is a schematic illustration of a MEMS chip sorter in a second position.

FIG. 2 is a plan view of the MEMS chip sorter 10 in the actuated position. In this position, the movable member or valve 110 is deflected upward into the position shown in FIG. 2. The diverting surface 112 is a sorting contour which redirects the flow of the inlet channel 120 into the sort output channel 122. The output channel 122 may lie in substantially the same plane as the inlet channel 120, such that the flow within the sort channel 122 is also in substantially the same plane as the flow within the inlet channel 120. There may be an angle cc between the inlet channel 120 and the sort channel 122. This angle may be any value up to about 90 degrees. Actuation of movable member 110 may arise from a force from force-generating apparatus 400, shown generically in FIG. 2. In some embodiments, force-generating apparatus may be an electromagnet, as described above. However, it should be understood that force-generating apparatus may also be electrostatic, piezoelectric, or some other means to exert a force on movable member 110, causing it to move from a first position (FIG. 1) to a second position (FIG. 2). The sort channel 122 may lead to a sort reservoir 22 which collects the sorted, target particles as effluent from the movable valve in the position shown in FIG. 2.

In some embodiments, the force generating apparatus 400 may include coils which generate a magnetic field, which then interacts with the movable member. In order to make the movable member responsive to such an electromagnetic force, it may have a magnetically permeable material inlaid into movable valve 110. The extent of this material may be to the edge, but just inside, the outline of 110 shown in FIGS. 1 and 2.

A magnetically permeable material should be understood to mean any material which is capable of supporting the formation of a magnetic field within itself. In other words, the permeability of a material is the degree of magnetization that the material obtains in response to an applied magnetic field.

The terms "permeable material" or "material with high magnetic permeability" as used herein should be understood to be a material with a permeability which is large compared to the permeability of air or vacuum. That is, a permeable material or material with high magnetic permeability is a material with a relative permeability (compared to air or vacuum) of at least about 100, that is, 100 times the permeability of air or vacuum which is about $1.26 \times 10^{-6}$ $H \cdot m^{-1}$. There are many examples of permeable materials, including chromium (Cr), cobalt (Co), nickel (Ni) and iron (Fe) alloys. One popular permeable material is known as Permalloy, which has a composition of between about 60% and about 90% Ni and 40% and 10% iron. The most common composition is 80% Ni and 20% Fe, which has a relative permeability of about 8,000. Accordingly, movable valve 110 may have permalloy material inlaid 116 into the movable feature 110 and subsequently planarized so that the profile of the movable valve remains flat. Additional details as to the fabrication of such permeable features may be found in the incorporated '095 patent application.

It is well known from magnetostatics that permeable materials are drawn into areas wherein the lines of magnetic flux are concentrated, in order to lower the reluctance of the path provided by the permeable material to the flux. Accordingly, a gradient in the magnetic field urges the motion of the movable member 110 because of the presence of inlaid permeable material 116, towards areas having a high concentration of magnetic flux. That is, the movable member 110 with inlaid permeable material 116 will be drawn in the direction of positive gradient in magnetic flux. A novel core design is described below with respect to FIG. 10a-10c, which concentrates the lines of flux in a very specific area, to optimize the control over the movable member 110.

Figure 3:
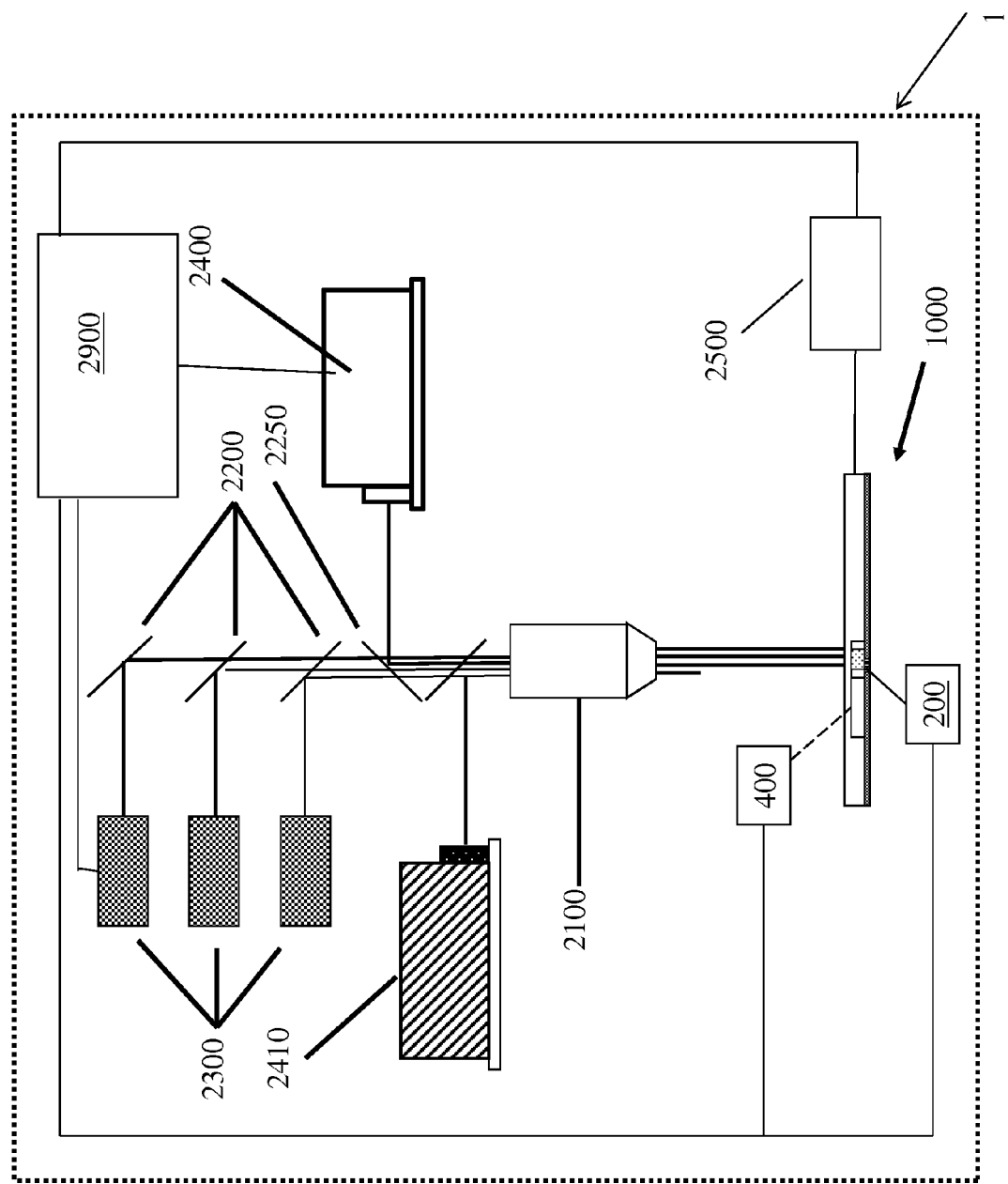
FIG. 3 is a schematic illustration of an exemplary MEMS cell sorting system which may make use of the MEMS sorter of FIGS. 1 and 2.

FIG. 3 is a schematic illustration of the cell sorting system 1 which may use microfluidic passageways, a MEMS chip sorter 10 housed in a disposable cartridge 1000, and a flux-generating apparatus 400. What follows is a description of some other components of the system and how they interact with the MEMS chip sorter 10. In particular, FIG. 3 lays out the optical path of the interrogating laser for interrogation region 200, and the control of fluid flow in channels 120-140 and control of MEMS chip sorter 10. After the system level description, the discussion will turn to the unique features of system 1 that allow the microfluidic system 1 to work in a precise, reliable and predictable way.

As shown in FIG. 3, the microfabricated MEMS chip sorter 10 may be housed in a disposable cartridge 1000, which may be loaded onto a movable stage and oriented with respect to detection optics and interrogating lasers 2400 in the cell sorting system 1. Fluid then flows through the MEMS chip sorter 10 from fluid reservoirs also housed in disposable cartridge 1000 through a series of passageways as will be described below with respect to FIGS. 4-8.

In the normal operation of system 1, the target particle may be a particular cell, such as a stem cell, or a cancer cell, which has been tagged with a fluorescent marker. This marker emits photons having a particular energy when irradiated with a laser 2400 operating at a predefined wavelength. Accordingly, in this cell sorting system, a laser source 2400 may be directed by a turning mirror 2250 through the detection/collection optics 2100 to the laser interrogation region 200 as was shown in FIGS. 1 and 2. The optical axis of the detection/collection optics 2100 and the laser source 2400 may be collinear, at least over a portion of the optical path. Thus, the orientation of the laser application and optical detection along this optical axis may be perpendicular or orthogonal to the substrate fabrication plane, orthogonal to the plane of motion of the movable valve 110 and orthogonal to the flow of the sample fluid through the detection region.

The fluorescence emitted from the irradiated particles may be shaped by detection/collection optics 2100 and separated by dichroic mirrors 2200 and directed into a bank of photodetectors 2300. A plurality of photodetectors may accommodate multiple wavelengths of emitted light, for multiparametric detection. The signal output by the photodetectors 2300 indicates the presence or absence of the target particle in the laser interrogation region 200. The signal may be delivered to a controller 2900, which manages the relative timing of the components in the particle sorting system 1, and collects the data. The controller 2900 may be a general purpose computer or a specialized circuit or ASIC. Upon detection of the target particle, a signal is generated by the controller 2900 which energizes the force-generating or flux-generating apparatus 400. The controller 2900 may also provide the fluidic control to the MEMS chip sorter 10, via one or more pneumatic, hydraulic, piston-based or mechanical force-based mechanisms which are illustrated generically by fluid control means 2500. The rate at which particles are detected may be monitored by the controller 2900, which may maintain the fluid control means 2500.

The force generating apparatus 400 is a device which causes a force to arise in the movable structure 110 itself, causing the motion of the movable structure. This force-generating apparatus 400 may not be directly mechanically coupled to the MEMS particle manipulation device 10, as indicated by the dashed line in FIG. 3. For example, the force-generating apparatus 400 may be a source of magnetic flux which causes a magnetostatic force to arise in an inlaid permeable material 116 in the MEMS movable valve 110 as described previously. Accordingly, flux generating apparatus 400 may be an electromagnet with a magnetic core and windings. This force may pull the movable valve 110 toward the force-generating apparatus 400, opening the sort channel 122 and closing the waste channel 140, as was shown in FIGS. 1 and 2. Importantly, the force-generating apparatus 400 may reside in the particle sorting system 1, rather than in the MEMS chip sorter 10. As mentioned previously, this may reduce the cost and complexity of the MEMS chip sorter 10, which may be housed in the disposable portion 1000 of the system 1. In the compact system shown in FIG. 3, it is important that excessive heat not be generated by force-generating apparatus 400. As mentioned previously, because of the very small size of MEMS chip sorter 10, force-generating apparatus 400 may also need to generate lines of flux which are concentrated in a small area. Details as to the design of a novel flux-generating apparatus 400 which may be suitable in this application are discussed below with respect to FIGS. 10a-10c.

Another optional laser 2410 may also be included to provide a second optical channel in cell sorting system 1. It should be understood that any number of laser sources 2410 may be used, but for simplicity of depiction, only two are shown in FIG. 3.

As mentioned, laser interrogation region 200 is the portion of the microfluidic passageway in which at least one laser 2400 is directed on the target particle, in order to distinguish it from the other constituents of the fluid sample.

Upon passing through the detection region 200, a signal may be generated by the detector 2300 indicating that a target particle is present in the interrogation region 200. After a known delay, a signal may be generated by the controller 2900 which indicates that the sorting gate, i.e. the movable valve 110 is to be opened, in order to separate the target particle which was detected, from the other components in the fluid stream. The movable MEMS valve 110 may comprise permeable magnetic materials 116 as mentioned previously, so that the magnetic force may arise in it in the presence of a magnetic field. When the signal is generated by the controller 2900, a force arises in the embedded magnetically permeable material 116 which draws the movable valve 110 toward the force generating apparatus 400. This motion may close off waste channel 140 and redirect the target particle into a sort channel 122. The sorted sample is subsequently collected from a sort reservoir at the end of the sort channel 122, which holds the sorted sample. As mentioned previously, the controller 2900 may also control flow rates based on the rate at which sorting events are recorded, or the control of flow rates may be based on some other feedback signal such as pressure or velocity, for example.

A fluid control means 2500 may control the direction and velocity of fluid flowing through the channels of the MEMS chip sorter 10. The fluid control means 2500 may be controlled based on a number of criteria as described below. The fluid control means 2500 may include pneumatic, hydraulic, and/or one way valves, and/or may include a piston or a pump and associated fluidic passages. During normal operation, the flow may be controlled by the fluid control means 2500 in a feedback loop with controller 2900 to keep cell velocity, fluid pressure, or event rate constant, for example.

In a further embodiment, the cell sorting system may comprise a feedback loop to prevent clogging of the channels by cells or other solid material suspended in the fluid. Biological cells especially tend to adhere at the channel surfaces, edges or offsets, thereby reducing the flow of liquid through the system and/or overall cell sorting performance. The feedback loop may consist of at least the fluid control means 2500, controller 2900 and a pump.

The controller 2900 may detect impending clogging by monitoring the fluid pressure and/or the cell velocity within the system. If the fluid pressure, the event rate and/or the average cell velocity fall outside a predefined range, it may be indicative of impending clogging. The controller 2900 may increase the pump rate until the fluid pressure and/or the cell velocity reaches the threshold again. The fluid pressure can be monitored by an appropriate detector, and cell velocity can be deduced by monitoring the event rate in the optical channel. Preferably, the cell speed may be between 0.2 and 10 m/s, and may be constant within +/−0.2 m/s. Accordingly the threshold activating the feedback loop may be a reduction of cell speed by around 0.2 m/s or the equivalent in loss of pressure. It should be understood that the details given here are exemplary only, and that the selection of such operating parameters will depend on the specifics of the application.

At the end of a sorting operation when the volume of sample to be sorted in nearly exhausted, the controller in concert with the fluid control means may reverse the flow of fluid in the microchannels, thus keeping the passages wet, as described in U.S. patent application Ser. No. 14/167,566, filed Jan. 29, 2014 and incorporated by reference in its entirety. The system 1 may also have the means to evaluate the effectiveness of the sorting process by reversing the flow through the laser interrogation region, as described in detail in U.S. patent application Ser. No. 13/104,084, filed Dec. 12, 2013 and incorporated by reference in its entirety.

What follows is a description of the enabling aspects of MEMS cell sorting system 1, in particular, what aspects allow the fluid to flow to and from MEMS chip sorter 10 in a repeatable and reliable way, from macroscopic reservoirs to the MEMS chip sorter 10, and to control the very small MEMS chip sorter 10.

Figure 4:
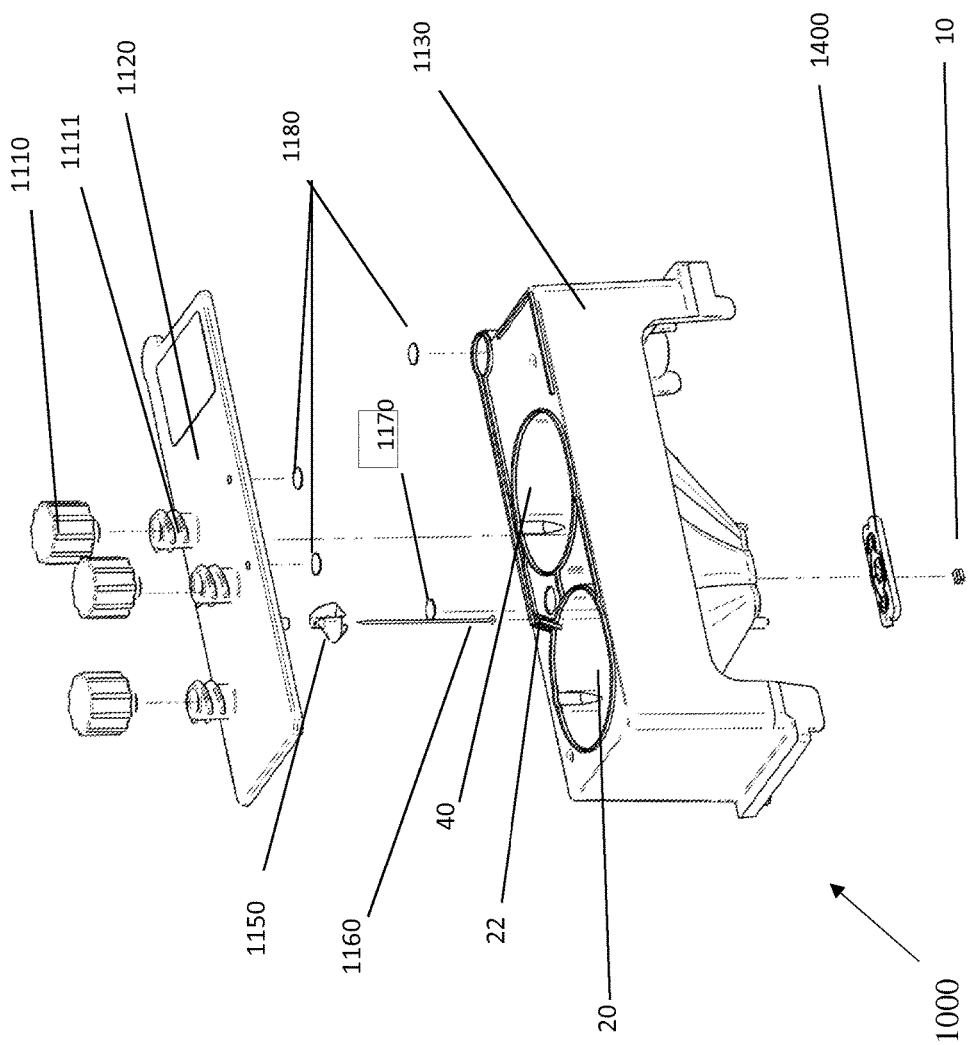
FIG. 4 is an exploded view of an exemplary disposable cartridge which may be used in the MEMS cell sorting system of FIG. 3, which includes a MEMS chip sorter and an interposer.

FIG. 4 is an exploded perspective view of an exemplary disposable cartridge 1000 which may be used in the particle sorting system shown in FIG. 3. Disposable cartridge 1000 may include several assemblable pieces, such as top 1120 and base 1130.

Disposable cartridge 1000 may house MEMS chip sorter 10 and provide storage in fluid reservoirs. Accordingly, the base 1130 of disposable cartridge 1000 may have a plurality of voids or compartments formed therein, including sample reservoir 20, sort reservoir 22 and waste reservoir 40. As described further below, the sample to be sorted may be stored in sample reservoir 20, the sort effluent in sort reservoir 22 and waste effluent in waste reservoir 40. The fluidic passageways between these voids may all be disposed in the interposer 1400 and/or in the MEMS chip sorter 10.

Between the top 1120 and the base 1130 may be disposed a number of filters 1180 to protect the sample from contamination or debris. These filters 1180 may be 0.20 micron Sterifilters, for example. The filters 1180 may be located directly above the various fluid reservoirs 20, 22 and 40.

Within the sample reservoir 20 and enclosed between the top 1120 and the base 1130 may be a magnetized propeller 1150, and a needle 1160 which may act as a shaft for magnetized propeller 1150. Upon exposure to a circulating magnetic field, magnetized propeller 1150 may rotate on shaft 1160, causing the contents of the sample reservoir 20 to be mixed or homogenized. Finally, a 20 micron filter 1170 may be placed over the sample reservoir 20, to filter the input sample before it heads downstream to the MEMS chip sorter 10.

Sample fluid may be introduced to the sample reservoir with a pipette, or with a syringe and plunger (not shown) through the access ports 1111 shown, whereupon the cartridge may be sealed with thumbscrews 1110. Alternatively, the cartridge may be delivered with the sample fluid already loaded therein.

Figures 5A, 5B:
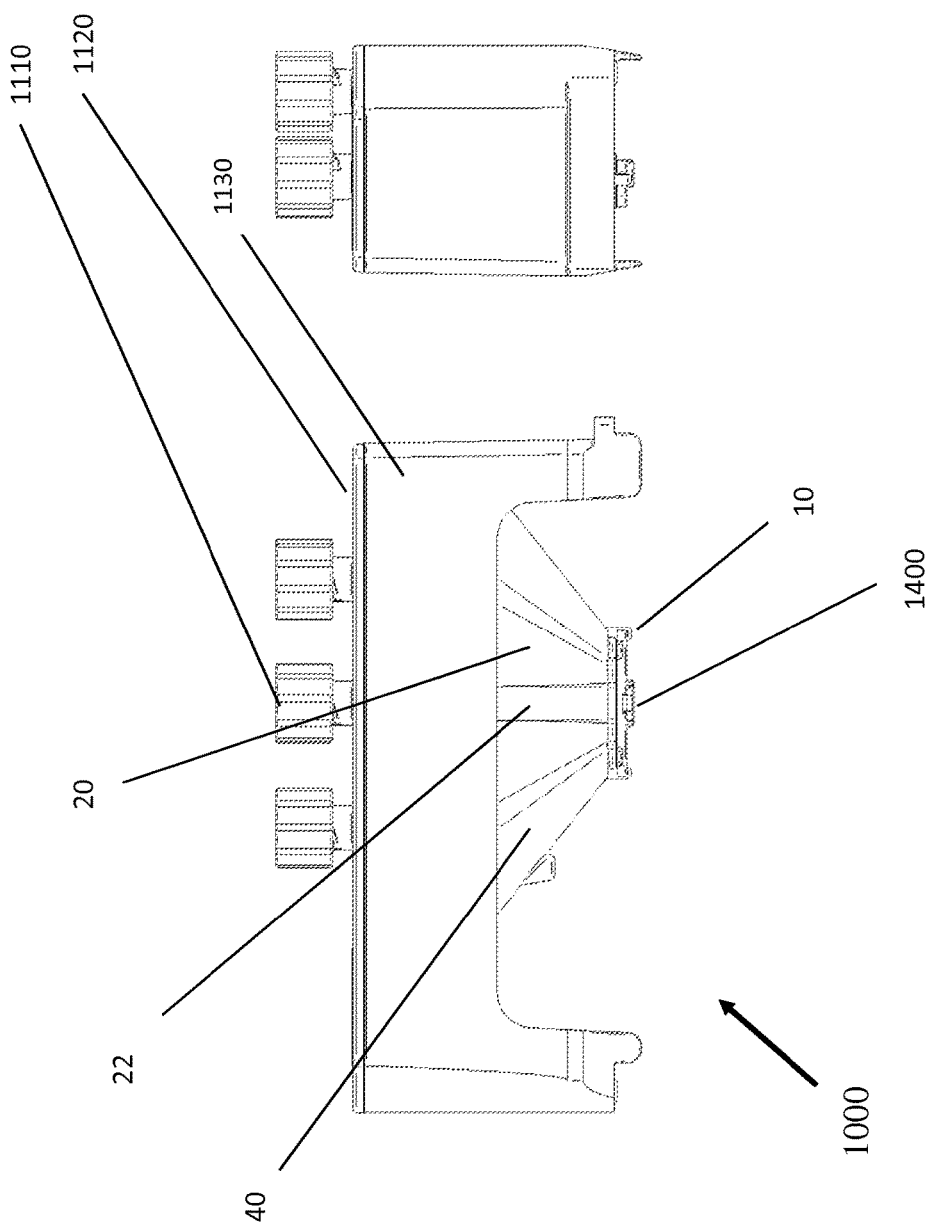
FIG. 5a is a side view of the exemplary disposable cartridge which may be used in the MEMS cell sorting system of FIG. 3, which includes a MEMS chip sorter and an interposer.
FIG. 5b is an end view of the exemplary disposable cartridge.

FIG. 5 is a side view of the assembled disposable cartridge 1000, showing the sample reservoir 20, sort reservoir 22 and waste reservoir 40. Shown in the assembled view are the relative locations of the MEMS chip sorter 10 and interposer 1400 with respect to the cartridge base 1130. It should be noted that FIG. 5 is inverted compared to FIG. 4, such that the sample reservoir 20, shown on the left hand side of the cartridge in FIG. 4, is now located on the right hand side in FIG. 5, as are the associated channels, stirrer, etc.

To provide a transition region between the very fine, microfabricated features of the MEMS chip sorter 10 and the much larger fluid volumes of reservoirs 20, 22 and 40, an interposer 1400 may be provided. The interposer 1400 may be formed from plastic by, for example, injection molding and may have intermediate tolerances on the order of +/−10 μm. The purpose of the interposer 1400 is to provide a transition between the very small structures of the MEMS device and the gross, macroscopic structures of the cartridge and reservoirs.

Because the interposer can be made with reasonably fine tolerances (+/−10 μm), it is possible to align the passages in the interposer 1400 with passages in the MEMS chip when the apertures to the channels are on the order of about 300 microns. While the widths of the channels leading to and from the movable valve 110 may be substantially smaller on the order of 150 microns, the apertures which introduce the fluid to the channels may be made near this scale. The holes are shown in FIG. 6.

Figure 6:
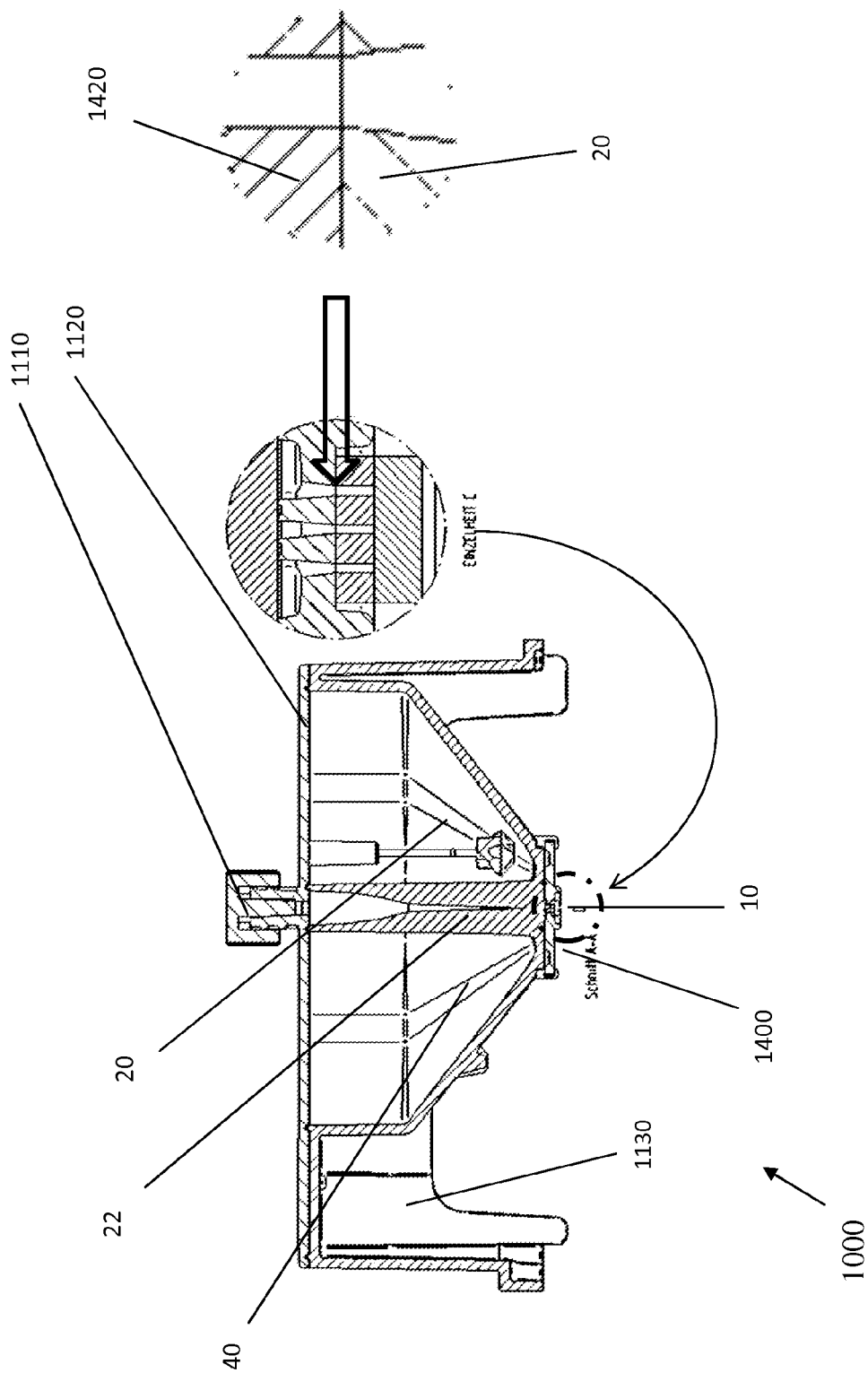
FIG. 6 is another side view of the exemplary disposable cartridge which may be used in the MEMS cell sorting system of FIG. 3, which includes a MEMS chip sorter and an interposer

As shown on the insert of FIG. 6, the through holes such as 1420 in interposer 1400 may have a tapered shape, with a diameter on the order of 300 microns at the top. This aperture may taper to a diameter of about 200 microns at the base where it meets the corresponding aperture of sort channel 20 of MEMS chip sorter 10.

Figure 7:
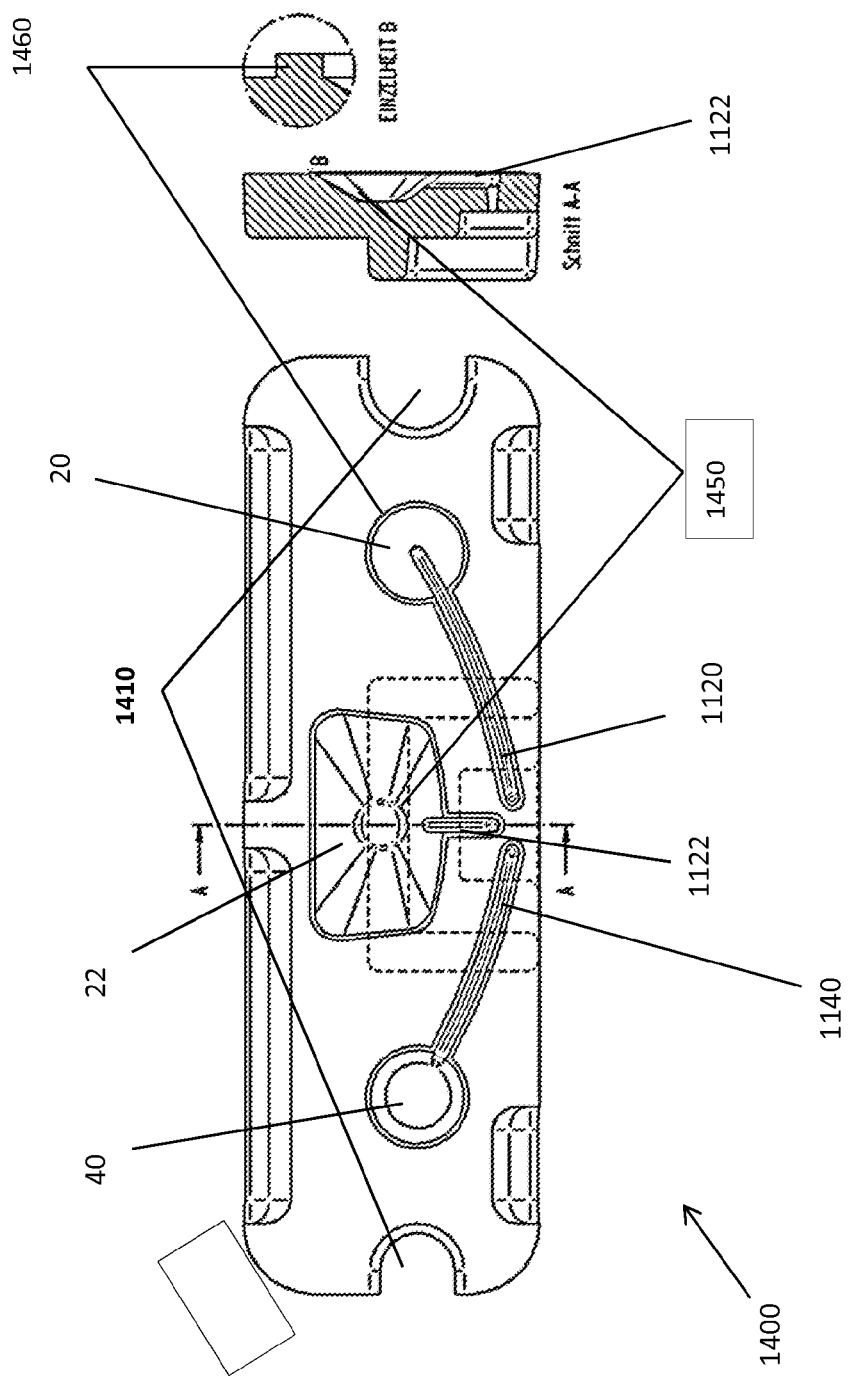
FIG. 7 is a plan view of an exemplary interposer which may be used with the disposable cartridge of FIG. 4.

The interposer may have passages formed therein, 1120, 1122 and 1140, shown in FIG. 7, which may correspond to channels 120, 122 and 140 shown in FIGS. 1 and 2. That is, passage 1120 may mate with passage 120 on MEMS chip sorter 10, to provide a fluidic pathway from sample reservoir 20 to MEMS chip sorter 10. Downstream of MEMS chip sorter 10, the interposer 1400 may provide a fluidic pathway from the movable valve 110 to the sort reservoir 22 (in cartridge) via sort channel 122 (on chip) and 1122 (on interposer). Similarly, the interposer 1400 may provide a fluidic pathway from the movable valve 110 to the waste reservoir 40 (in cartridge) via waste channel 140 (on chip) and 1140 (on interposer).

Another purpose of the interposer is to provide a collection region for possibly small volumes of sorted material. For example, since the target cells may be rare, such as stem cells, the volume of fluid collected in the sort reservoir may also be rather small, and in proportion to the frequency of target cells in the sample. Accordingly, volumes as low as a few microliters may be expected. The interposer may provide a region into which the sorted effluent is siphoned, for easy collection with a small pipette. This siphon region is shown in FIG. 7.

In particular, it should be noticed that the floor of siphon region 1450 is at a lower elevation than the bottom of the sort channel 1122. Accordingly, fluid may flow as assisted by siphoning action and meniscus forces from the MEMS chip sorter 10 to the sort reservoir, from which it can be retrieved by hypodermic needle or micropipette. This siphoning may help offset the capillary forces that may occur from small volume flow in the very small channels.

Importantly, the sort channel 1122 may be made relatively short compared to sample channel 1120 and waste channel 1140, so that the amount of material lost by adhesion to channel walls, for example, is minimized.

Also shown in the detail of FIG. 7 is a glue dam 1460, which will be described next with respect to cartridge assembly.

As can be seen in FIG. 7, the sample channel 1122 may draw material from the very bottom of the sample reservoir 20. This may be important in maximizing the yield, or percent of recovered material, from a given sample volume. In contrast, the waste channel 1140 may deliver the non-target material to a point on the incline of the wall of the waste void or reservoir 40.

The interposer 1400 may be made from The interposer 1400 may be made from polycarbonate, polymethyl methacrylate (PMMA), cyclic olefin polymer (COP), or other materials, by injection molding, embossing, laser machining or 3D printing. The tolerances on the passages 1420 in the interposer 1400 may be about +/−10 microns on a total diameter of about 100 to 400 microns. The corresponding passages 20 in the MEMS chip sorter 10 may be about 50 to 150 microns. These passages 20 and 1420 may then be aligned as was shown in the insert to FIG. 6. to within about 10 microns. The MEMS chip sorter 10 may first be glued to the interposer by seating it in the chip cavity 1470 shown in FIG. 9. The cavity 1470 may be formed sufficiently precisely that the passages in MEMS chip sorter 10 roughly overlap the passages in interposer 1400. The allowed mismatch may be up to about 20 microns, easily achievable. A pick and place machine, well known in printed circuit board manufacturing, may be adequate for this task. The MEMS chip sorter 10 may be glued in place within cavity 1470.

Figure 8:
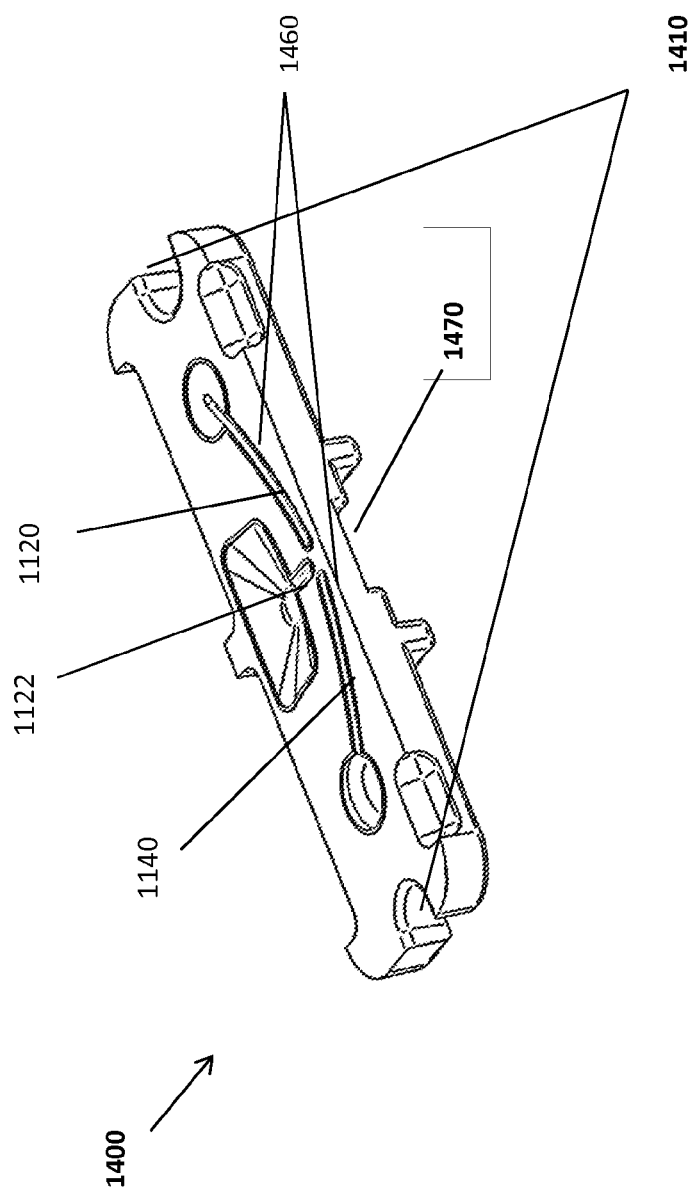
FIG. 8 is a perspective view of the exemplary interposer which may be used with the disposable cartridge of FIG. 4, showing the cartridge-facing side.

The interposer 1400 may then be glued to the cartridge base 1130 with glue or cement, by locating the interposer 1400 locating holes 1410 against corresponding posts in cartridge body 1000. Since this glue or cement will be required to be watertight, yet not interfere with passages 1120, 1122 or 1140, some features may be formed as glue dams 1460 around these channels, as shown in FIGS. 7 and 8. These glue dams 1460 may serve to keep the liquid, uncured glue from entering the small channels 1120, 1122 and 1140. The features 1460 may be raised ridges of plastic material which prevent the liquid from entering the channels or other depressions. In particular, glue may be injected into a port that gives access to the interface between interposer 1400 and the remainder of cartridge body 1000. The glue will wick around this area but may be kept out of microfluidic passageways 1120, 1140 and 1122 by glue dams 1460 that surround these passageways are shown in FIG. 7 and in the perspective drawing of FIG. 8. The glue dams reduce the thickness of the interface between interposer 1400 and the remainder of cartridge body 1000 from about 50 µm to 0.2 to 2 µm thereby creating a capillary effect that prevents the glue from flowing beyond the dam into the microfluidic passageways. It should be understood that these dimensions are exemplary only, and that such details will depend on the specifics of the application. Depending on the type of glue used, the liquid glue may be cured by heat, pressure or exposure to UV radiation, for example.

Alternatively, the interposer 1400 may be bonded first to the cartridge body 1000, and then the MEMS chip sorter 10 may be added to the assembly.

FIG. 9 is a simplified perspective view of the obverse side of the interposer 1400. This side includes the seating area 1470 for MEMS chip sorter 10. The MEMS chip sorter 10 may be glued or otherwise bonded against the features of seating area 1470.

Exemplary dimensions for the interposer are 16 mm length, 6 mm width, 1 mm height. The waste and sample reservoirs may be 2 mm in diameter. The sample channel 1120, sort channel 1122 and waste channel 1140 may each be 300 microns in width. The height of the glue dams may be about 20 microns.

Accordingly, a manufacturing process for the cartridge 1000 may include:

1) Glue MEMS chip sorter 10 to interposer 1400
2) Place interposer against cartridge locating pins
3) Press interposer
4) Introduce glue to gaps between interposer and cartridge
5) UV cure glue
6) Attach cartridge base to cartridge top by glue, cement, or ultrasonic welding, for example It should be clear that steps 1-6 need not be executed in the order shown. For example, the cartridge base 1130 may be attached to the cartridge top 1120 before attaching the MEMS chip 10 or interposer 1400.

Figure 12:
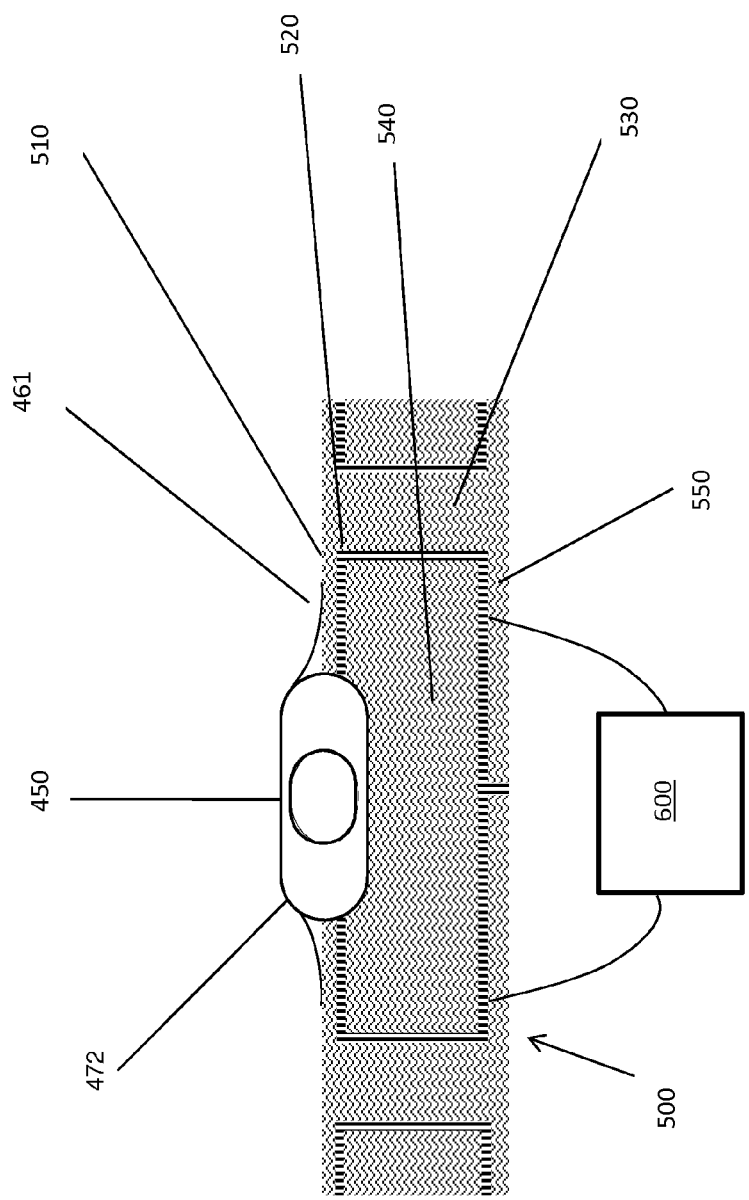
FIG. 12 is a top-down view of another embodiment of the targeted electromagnet that may generate the magnetic field which use a copper printed circuit board for heat sinking.

As described previously, the actuation mechanism in the system shown in FIG. 3 may be electromagnetic. Therefore, another aspect of the system described above with respect to FIGS. 1, 2 and 3 is the need for a precisely localized magnetic field which will actuate the small, MEMS chip sorter 10. Because the movable valve 110 is so small, it is important to have the flux-generating structure be precise, low power and efficient. Accordingly, the MEMS-based cell sorting system may include an electromagnet that generates a very localized magnetic field to actuate the MEMS chip sorter 10. The electromagnet may also be designed to have adequate thermal properties, so that it can operate reliably for long periods of time at high speed. Details of the design are shown in FIGS. 10-12, and described further below.

The external source of magnetic field lines (magnetic flux) may be provided outside the MEMS chip sorter 10, as was shown in FIGS. 1 and 2. This source may be an electromagnet 400. The bare electromagnet 400 is shown in greater detail in FIGS. 10a-10c. FIG. 10a shows a side view of the electromagnet 400; FIG. 10b shows a zoomed-in top view of the electromagnet 400; and FIG. 10c shows perspective view of the electromagnet 400. The electromagnetic with heat sinking material is shown in FIGS. 11a, 11b and 11c. The electromagnet with a copper pcb is shown in FIG. 12.

The electromagnet 400 may include a permeable core 470 around which coils 460 are wound. The core 470 may have a projecting tapered portion 472 and a flattened tab portion 474. The projecting tapered portion 472 may have a widened base 452 which tapers to a narrow tip 450, as shown in FIG. 10b. The coils 460 may be wrapped around the tapered portion 472, but not the flattened tab portion 474, for example. The flattened tab portion 474 may serve primarily to provide a low reluctance path to close the lines of flux generated by the coil. Although FIG. 10a shows the coils 460 wrapped only around the tapered shape 472, the coils may be placed in other locations, such as around other parts of the magnetic core 470. The coils 472 may be placed around the widened tab 474, for example, instead of or in addition to, coils wrapped around the tapered shape 472.

For clarity, the coils 460 are not shown in FIG. 10b, which instead shown greater detail of the tapered portion 472.

The coils 460 and core 470, with taper 472 and tab 474, generate a magnetic field which exits the pole of the electromagnet 400 at the tip 450, diverges, and returns to the opposite pole, as is well known from elementary electromagnetism. When the electromagnet 400 is brought into the vicinity of the movable valve 110, and the coil 460 is energized, the coil 460 and magnetic core 470 generate lines of flux that diverge strongly from the tip 450. Accordingly, the movable member 110 is generally drawn toward the tip 450 of the electromagnet 400 as shown in FIG. 10a, because the permeable material 116 inlaid therein is drawn into areas of increasing flux density. Electromagnet 400 may therefore act as a bar magnet, where the coil is wrapped around a simple bar of permeable material, such that a magnetic dipole arises in the bar, with lines of flux emanating from the north pole and returning (in the far field) to the south pole.

The tip 450 may be shaped so that the magnetic field is focused, increasing the magnetic field strength up toward the magnetic saturation limit, and launching it effectively into the permeable element in the MEMS chip sorter 10, which was described previously as the inlaid permeable material 116. The inlaid permeable material may be a thin film, wherein the thickness of the film is relatively small compared to a lateral extent. As a result, the tip 450 may have one dimension larger than the other, to provide a field of flux that couples effectively into the inlaid permeable material 116. The permeable feature 116 will then be drawn towards regions of increasing flux concentration, which is toward the tip 450.

As shown in FIG. 10a, the magnetic core 470 may be given a tapered shape, 472 which may tend to further concentrate the magnetic flux in the region around the tip

450. The angle α of the taper may be, for example, between about 0 and to about 30 degrees from vertical. The aspect ratio (length of taper/average width of taper) may be less than around 5/1, and more preferably around 2/1 for example, but may be designed in a broad range of shapes. In order to focus the flux at the tip 450, however, it may be advantageous to have the diameter at the tip be less than the diameter at the base of the tapered shape. FIG. 10*b* is an enlarged, top-down view of the tip of magnetic core 470, showing the tapered shape of the tip, face-on. The tapered shape 472 may have a contour that is narrower at the tip 450 than at the base, 452. The tapered shape 472 may be pyramidal, for example. Although the tip 450 and base 452 are shown as generally oblate, it should be understood that this is exemplary only, and that tip 450 and base 452 may have any arbitrary shape, but the tip 450 has at least one lateral dimension which is smaller than the base, 452. In other words, the tapered shape 472 may be a geometrical body having an aspect ratio of length:width between 1:1 to 5:1, a smaller diameter at the top than at the base with a taper angle between about 3° and about 45°.

FIG. 10*c* is a perspective view of the tapered shape 450, coils 460 and magnetic core 470. The base 452 of the taper 472 may have a width of less than about 5 mm, and a tip 450 of less than about 1 mm across a widest chord. The height of the tapered shape 472 may be less than about 10 mm. Accordingly, the tapered shape may have a contour that forms an angle α of at least about 3 degrees and at most about 45 degrees, with the angle defined with respect to the symmetry axis as illustrated in FIG. 10*a*. More specifically, the contour may form an angle α of about 10 degrees with respect to the symmetry axis.

More preferably, the base of the tapered shape may have a height of 2 to 5 mm and a width of 0.5 to 2 mm at the base. The tip 450 of the tapered shape may be smaller than the base 452 and may have rectangular dimensions of about 1.0 mm×0.7 mm, or at least about 0.2 mm×0.1 mm. It should be understood that these dimensions are exemplary only, and that such details will depend on the specifics of the application. Magnetic modeling suggests that a electromagnet tip of the approximate width of the permeable elements in the MEMS chip sorter 10 is optimal, with a height of approximately the same order of magnitude. The base size is then determined by the taper angle.

The magnetic core 470 with tapered shape 472 may further comprise a widened tab portion 474 at the base of the tapered shape 472, wherein the widened tab 474 has an extent in the longest dimension of about 10 mm. As described further below, the magnetic core 470 with the tapered shape 472 and widened tab 474 may be in contact with a heat sinking material on at least two sides.

The magnet material of the core 470 may be a cobalt/iron, iron, a nickel/iron alloy, or any other highly permeable magnetic material. In some embodiments, the magnet material 470 may be a NiFe Permalloy (70% Ni and 30% Fe). The material may have a permeability of at least about 5000.

Magnetic modelling also shows, and experiment confirms, that the width W of the tab portion 474 may be important in reducing the overall reluctance of the magnetic path. A tab 474 portion width of about 10 mm has been shown to perform acceptably.

To generate as large a field as possible requires the application of as much current, through as many turns as possible, to the tapered magnetic element 472 and coil 460. However, as is well known, large currents through small diameter wires can generate substantial heat, which can degrade or even destroy the device. It is important, therefore, to get the heat away from the delicate structures as expeditiously as possible.

In general, there may be a trade-off between fewer layers of coils 460 for more effective heat dissipation, or more layers for greater flux (Amp*turn), and thus greater magnetic force and higher speed. In one embodiment, the coils 460 around the tapered magnet 472 have one layer, but in other embodiments, the electromagnet 400 may have more, and up to at least three layers of coils is envisioned on the taped magnetic element 472.

But because the form factor of all these elements in necessarily small, the wire diameter must be relatively small in order to maximize the number of turns which can be would around the tapered magnetic element 472. The smaller wire size tends to increase the resistance and thus the power generated in the wire. This situation leads to a substantial amount of Joule heating, such that heat-sinking the apparatus becomes an important design consideration.

FIG. 11*a* shows a side view of the electromagnet 400 with heat sinking 440 applied thereto. FIG. 11*b* shows a top view of the electromagnet 400 with heat sinking 440 applied thereto. FIG. 11*c* shows perspective view of the electromagnet 400 with heat sinking 440 applied thereto. FIG. 11*a* shows that the electromagnet is surrounded on all sides by a heat sinking material 440. In fact, the magnetic core 470 with the tapered shape 472 may be surrounded laterally by a heat sinking material, so that gaps between the heat generating solenoid coils 460 and the heat sinking material 440 are reduced or minimized. The heat sinking material 440 may have high thermal conductivity, and may also be electrically conductive, as many high thermal conductivity materials are. The heat sinking material 440 may be, for example, copper, steel, aluminum, or any other material with adequate heat conductivity, and which may be formed into the desired shape. Again to reduce air gaps between the solenoid coils 460 and the heat sinking material 440, a thermally conductive paste or grease or potting compound may be applied to the solenoid coils 460. Alternatively, the solenoid and tapered shape 472 may be pressed into a malleable material, such as Indium, which melts at a low temperature and is relatively soft in the solid state. In any case, the tapered shape 472 may be surrounded laterally by a heat sinking material. In one embodiment, the tapered shape 472 and the tab 474 are in contact with the heat sinking material on at least two sides.

As illustrated in FIG. 11*a*, the current in the solenoid around the tapered magnetic element 472 and 460 gives rise to a magnetization in the material which then emits lines of magnetic force 442 which emerge from the tip 450 and close on themselves through the base 470. The lines are concentrated at the tip 450, drawing the inlaid magnetic material 116 in the MEMS chip 10 toward the tip 450, as explained earlier. However, for high speed actuation of the MEMS chip 10, it is required that the magnetic field 442 be turned off and on rapidly. This rapidly changing magnetic field may give rise to eddy currents 444 in the heat sinking material 440. These eddy currents 444 by their nature oppose the magnetic field, which may degrade the performance of the electromagnetic solenoid 460 at high speeds.

To reduce this eddy current effect, an insulator structure 480 may be placed in the heat sink material 440 which will interrupt the eddy current flow 444. The insulator structure 480 may be an epoxy, a glue, an oxide or a nitride for example, which may be deposited or applied in the heat sink material 440. The eddy currents 444 and insulator 480 are shown in FIG. 11*b*.

The insulator structure 480 may be disposed in a number of ways, to impede the flow of eddy currents 444 in the heat sinking material 440 in response to the magnetic flux generated by the electromagnet. In one embodiment, the insulator structure 480 in the heat sinking material is disposed adjacent to the base of the taper 452, and between the heat sinking material 440 and the magnetic core 470, as shown in FIG. 11a. In another embodiment, the insulator structure 480 in the heat sinking material 440 is disposed laterally and along a symmetry axis 492 of the tapered shape 472, as also shown in FIG. 11b. It should be understood that the insulator structure 480 shown in FIGS. 11a and 11b are exemplary only, and that the insulator structure 480 may be placed in other locations as well, to impede the flow of eddy currents 444. In any case, the heat sinking material may include an insulator structure which impedes the flow of eddy currents in the heat sinking material in response to the magnetic flux generated by the electromagnet.

In one embodiment, the solenoid of coils 460 comprises between about 20 and about 30 turns of wire wound around the tapered shape. In one particular embodiment, the solenoid may include 28 turns of the wire on the magnetic core. The solenoid of coils may be comprised of magnet wire of a diameter of about 100 microns. The magnet wire may carry a current of at least about 0.5 A, to generate a magnetic field of 1.6 Tesla emerging from the tip of the coil.

FIG. 12 shows another approach to the heat sinking design which may address wire bonding issues as well. In particular, the tapered shape 460 may be embedded in a copper-based printed circuit board (PCB) 500. The copper PCB 500 may have a copper core 540, surrounded by copper vias 530 which connect a upper copper conductive pads 510 to lower copper conductive pads 550. These vias 530 may be surrounded by an insulating material 520, which isolates electrically the upper conductive pads 510 from the vias 530 and lower conductive pads 550. The insulating material 520 may be an epoxy or oxide or nitride which may be grown or deposited on the copper.

The copper PCB 500 may be shaped or machined to accept the contour of the taper 460 with a close-fitting surface, such that only the tip 450 of the taper 460 is exposed. The solenoid wires 461 may be soldered to the upper conductive pads, so that the copper PCB also provides a convenient interface between the very fine magnet wire of the solenoid with the larger wires coming to and from the current driver 600. The electrical connections to the current driver 600 to the tapered solenoid 460 may therefore be made through wires to the lower conductive pads 550, through the vias 530 and on to the upper conductive pads to wires 461 to the solenoid. Thus, the copper PCB 500 may provide both heat sinking and convenient electrical structures for the device.

Accordingly, the cell sorting system for sorting target particles from a fluid sample may include a copper printed circuit board. The PCB may include a copper core, and a plurality of upper and lower conductive pads, wherein the upper and lower conductive pads are electrically connected by a conductive via. The copper PCB may also be configure such that the ends of the solenoid coil are electrically connected to the plurality of upper conductive pads, and wherein lower conductive pads are electrically connected to a current driver. The plurality of upper and lower conductive pads, are insulated from the copper coil by an insulating material.

It should be understood that the use of the insulator 480, copper PCB 500, and other features described herein are optional features of some embodiments, and may not be necessary to practice this invention. "Magnet wire" as used above, should be understood to mean, a fine copper or aluminum wire coated with a very thin layer of insulation. Magnet wire is typically used for coils in the construction of transformers, inductors, motors, speakers or other devices requiring large numbers of conductor turns in a small space. It should also be understood that spatial designations such as "upper" and "lower" are arbitrary, and the invention does not depend on the orientation of the device. In some embodiments, the upper and lower conductive pads may be disposed on obverse sides of the copper PCB. The solenoid wires may be electrically connected to one set of pads, for example, the upper pads, and a current driver may be electrically connected to a set of pads on the obverse side, for example, the lower pads, or vice versa.

Accordingly, while various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Furthermore, details related to the specific methods, dimensions, materials uses, shapes, fabrication techniques, etc. are intended to be illustrative only, and the invention is not limited to such embodiments. Descriptors such as top, bottom, left, right, back front, etc. are arbitrary, as it should be understood that the systems and methods may be performed in any orientation. Accordingly, the exemplary implementations set forth above, are intended to be illustrative, not limiting.

What is claimed is:

1. A cell sorting system for sorting target particles from a fluid sample, comprising:
   a cell sorting valve microfabricated on a silicon substrate with microfabricated channels leading from the cell sorting valve, wherein the cell sorting valve separates the target particles from non-target material;
   a disposable cartridge containing a sample reservoir, a sort reservoir and a waste reservoir; and
   an electromagnet having coils and a single magnetic core having a tapered shape, which concentrates magnetic lines of flux at a tip of the tapered shape, the core constituting a bar dipole having a north pole and a south pole, wherein the electromagnet produces lines of magnetic flux in a region adjacent to the cell sorting valve, causing the cell soiling valve to move in response to lines of flux produced by the electromagnet, wherein lines of flux exit from the north pole and return to the south pole of the magnetic core, wherein the cell sorting valve redirects the target particles from a sample inlet channel into one of a plurality of output channels, and wherein motion of the cell sorting valve is substantially in a first plane parallel to a surface of the substrate; wherein a sample inlet channel is substantially also in the first plane parallel to the surface of the substrate, and wherein at least one of the output channels is in a second, different plane than the cell sorting valve and the sample inlet channel.

2. The cell sorting system for sorting target particles from a fluid sample of claim 1, wherein the coils of the electromagnet are wrapped around the tapered shape, such that the coils and the core of the electromagnet have a tapered shape and the electromagnet is separate from the substrate.

3. The cell sorting system for sorting target particles from a fluid sample of claim 2, wherein the electromagnet comprises a solenoid of coils wrapped around a magnetic core having a tapered shape, wherein the tapered shape has a contour which narrows from a base to a tip.

4. The cell sorting system for sorting target particles from a fluid sample of claim 3, wherein the tapered shape has a base of less than about 5 mm and a tip of less than about 1 mm across a widest chord.

5. The cell sorting system for sorting target particles from a fluid sample of claim 3, wherein the contour forms an angle of about 10 degrees, with the angle defined with respect to vertical.

6. The cell sorting system for sorting target particles from a fluid sample of claim 3, wherein the contour forms an angle of at least about 3 degrees and at most about 45 degrees, with the angle defined with respect to vertical.

7. The cell sorting system for sorting target, particles from a fluid sample of claim 3, wherein the magnetic core having the tapered shape comprises at least one of a cobalt/iron, iron, and nickel/iron alloy.

8. The cell sorting system for sorting target particles from a fluid sample of claim 3, wherein the solenoid of coils comprises between about 20 and about 30 turns of wire wound around the tapered shape.

9. The cell sorting system for sorting target particles from a fluid sample of claim 3, wherein the solenoid of coils comprises magnet wire of a diameter of about 100 microns.

10. The cell sorting system for sorting target, particles from a fluid sample of claim 3, wherein the solenoid of coils conducts a current of at least about 0.5 A.

11. The cell sorting system for sorting target particles from a fluid sample of claim 3, wherein the electromagnet further comprises widened tab at the base of the tapered shape, wherein the widened tab has an extent in the longest dimension of about 10 mm.

12. The cell sorting system for sorting target particles from a fluid sample of claim 1,
wherein the tapered shape is surrounded laterally by a heat sinking material wherein the coils of the electromagnet are wrapped around the tapered shape, such that the coils and the core of the electromagnet form a solenoid of coils having a tapered shape and the electromagnet is separate from the substrate.

13. The cell sorting system for sorting target particles from a fluid sample of claim 12, wherein the tapered shape and the tab are in contact with the heat sinking material on at least two sides.

14. The cell sorting system for sorting target, particles from a fluid sample of claim 13, wherein the heat sinking material comprises copper.

15. The cell sorting system for sorting target particles from a fluid sample of claim 13, further comprising a copper printed circuit board.

16. The cell sorting system for sorting target particles from a fluid sample of claim 15, wherein the copper printed circuit board comprises a copper core, and a plurality of upper and lower conductive pads, wherein the upper and lower conductive pads are electrically connected by conductive vias.

17. The cell sorting system for sorting target particles from a fluid sample of claim 16, wherein ends of the solenoid of coils are electrically connected to the plurality of upper conductive pads, and wherein lower conductive pads are electrically connected to a current driver.

18. The cell sorting system for sorting target particles from a fluid sample of claim 16, wherein the vias, and the plurality of upper and lower conductive pads, are insulated from the copper coil by an insulating material.

19. The cell sorting system for sorting target particles from a fluid sample of claim 12, wherein the heat sinking material comprises an insulator structure which impedes the flow of eddy currents in the heat sinking material in response to the magnetic flux generated by the electromagnet.

20. The cell sorting system for sorting target particles from a fluid sample of claim 19, wherein the insulator structure in the heat sinking material is disposed adjacent to the base of the taper.

\* \* \* \* \*